(12) United States Patent
Abir

(10) Patent No.: US 9,844,338 B2
(45) Date of Patent: *Dec. 19, 2017

(54) BREASTFEEDING QUANTITY ESTIMATOR

(71) Applicants: Digisense Ltd., Petach Tikva (IL); Expro3, LLC, Coral Gable, FL (US)

(72) Inventor: Eyall Abir, Petach Tikva (IL)

(73) Assignees: Digisense Ltd., Petach Tikva (IL); Expro3, LLC, Coral Gable, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/177,803

(22) Filed: Jun. 9, 2016

(65) Prior Publication Data
US 2017/0007179 A1   Jan. 12, 2017

Related U.S. Application Data

(63) Continuation of application No. 14/692,306, filed on Apr. 21, 2015, now Pat. No. 9,380,977, which is a continuation of application No. PCT/IL2013/050833, filed on Oct. 16, 2013.

(51) Int. Cl.
| | |
|---|---|
| *A61B 5/00* | (2006.01) |
| *A61F 13/42* | (2006.01) |
| *A61F 13/49* | (2006.01) |
| *A61B 90/30* | (2016.01) |

(52) U.S. Cl.
CPC .......... *A61B 5/4866* (2013.01); *A61B 5/0077* (2013.01); *A61B 5/4288* (2013.01); *A61B 5/4875* (2013.01); *A61B 5/6808* (2013.01); *A61B 5/7278* (2013.01); *A61B 5/742* (2013.01); *A61B 5/746* (2013.01); *A61B 90/30* (2016.02); *A61F 13/42* (2013.01); *A61F 13/49* (2013.01); *A61B 2090/309* (2016.02); *A61F 2013/424* (2013.01)

(58) Field of Classification Search
None
See application file for complete search history.

(56) References Cited

U.S. PATENT DOCUMENTS

| | | | | |
|---|---|---|---|---|
| 2005/0283327 | A1* | 12/2005 | Bowman | G06F 19/3475 702/81 |
| 2006/0253064 | A1* | 11/2006 | Gelfand | A61B 5/201 604/31 |
| 2008/0051745 | A1* | 2/2008 | Long | A61F 13/42 604/361 |

(Continued)

*Primary Examiner* — Travis Hunnings
*Assistant Examiner* — Chico A Foxx
(74) *Attorney, Agent, or Firm* — Greenberg Traurig, LLP

(57) ABSTRACT

A sensor for indirect estimation of breast milk intake by an infant, the sensor comprising: a housing configured to be externally attached to an incontinence product worn by a subject, said housing comprising: a light-emitting diode (LED) configured to illuminate the incontinence product; a photodetector configured to output an indication of the amount of light reflected from the incontinence product; and an integrated circuit configured to: (a) receive the indication from said photodetector, (b) compute, based on the indication, an amount of urine secreted by the subject into the incontinence product, and (c) estimate the amount of breast milk intake by the infant based on the amount of urine secreted by the subject into the incontinence product.

14 Claims, 11 Drawing Sheets

(56) References Cited

U.S. PATENT DOCUMENTS

| | | | |
|---|---|---|---|
| 2008/0266117 A1* | 10/2008 | Song | A61F 13/42 340/573.5 |
| 2010/0168694 A1* | 7/2010 | Gakhar | A61F 13/42 604/361 |
| 2010/0168702 A1* | 7/2010 | Ales | A61F 13/42 604/361 |
| 2012/0116337 A1* | 5/2012 | Ales | A61F 13/42 604/361 |
| 2012/0161960 A1* | 6/2012 | Cheng | A61F 13/42 340/539.12 |
| 2014/0121487 A1* | 5/2014 | Faybishenko | A61B 5/157 600/365 |
| 2014/0137015 A1* | 5/2014 | Gurtler | G06F 3/03542 715/765 |
| 2015/0009502 A1* | 1/2015 | Drury | G01N 33/493 356/422 |

* cited by examiner

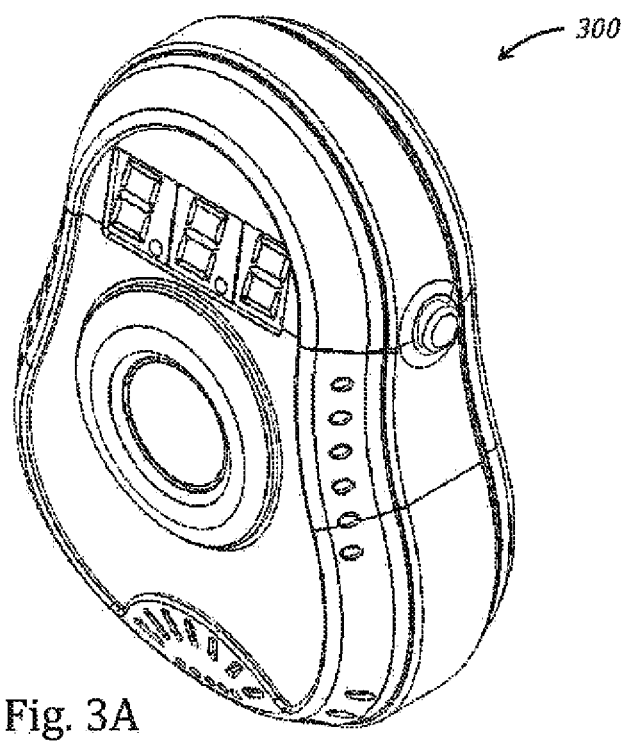
Fig. 3A
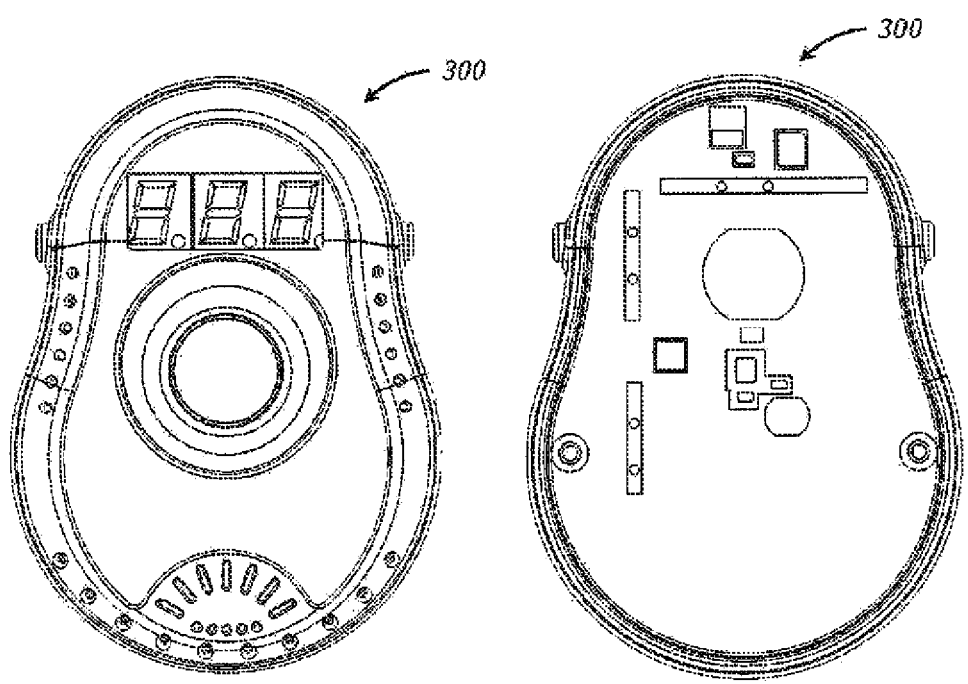
Fig. 3B
Fig. 3C

BREASTFEEDING QUANTITY ESTIMATOR

CROSS REFERENCE TO RELATED APPLICATIONS

This application is a continuation of U.S. patent application Ser. No. 14/692,306, filed on Apr. 21, 2015, which is a continuation of International Patent Application Serial No. PCT/IL2013/050833, filed on Oct. 16, 2013, which claims priority to U.S. Provisional Patent Application Ser. No. 61/716,767, filed on Oct. 22, 2012, the entire contents of which are hereby incorporated by reference in their entirety.

FIELD OF THE INVENTION

Some embodiments relate to a breastfeeding quantity estimator.

BACKGROUND

Breastfeeding is recommended by the American Academy of Pediatrics, the World Health Organization and medical professionals worldwide as the preferred method for feeding infants during the first year of life. Human breast milk has significant health benefits that, to date, cannot be replicated by infant formula. Specifically, breast milk has been shown to reduce the incidence of infectious diarrhea, respiratory infections, otitis media, childhood obesity and other conditions. Breastfeeding has been shown to have health benefits for mothers too, such as by reducing the risk of postpartum bleeding and anemia. Risks are also lowered for ovarian and premenopausal breast cancer. Further, postpartum weight loss is enhanced in breastfeeding mothers. Other benefits of breastfeeding include its comforting effect upon both mother and infant. For these reasons, many health professionals feel that breastfeeding produces healthier, happier, infants and mothers, which is why breastfeeding is being promoted worldwide as a public health measure.

The need to know the amount of breast milk suckled by an infant is important to many lactating mothers. This information may help evaluate the infant's nutritional status, the need for breastfeeding guidance, and/or the use of infant formula, and is therefore important to the pediatrician as well. It is accepted that normal breast milk intake of an average infant starts at a few dozen milliliters during its first day of life, increases to a few hundred milliliters a day during the first week of life, and can reach approximately 700-900 milliliters per day afterwards. See J. Riordan and K. Wambach, "Breastfeeding and Human Lactation", Jones & Bartlett Publishers, $4^{th}$ ed. (2009).

Many mothers, due to their false impression and worry that insufficient milk is consumed by the infant, choose to discontinue breastfeeding fully or partially, and start using formulas. This is an unfortunate situation.

Devices for measuring the amount of milk expressed during breastfeeding have been proposed in the past. Many such devices adopt methods of fluid flow measurement, and typically include a flow or capacity meter mounted on the breast during breastfeeding, to measure the amount of milk flowing through. A few examples of such devices are shown in U.S. Pat. No. 5,827,191 to Rosenfeld, U.S. Patent Application Publication No. 2008/0039741 to Shemesh et al., and U.S. Patent Application Publication No. 2005/0177099 to Dahan. Other devices propose the use of flow gauges utilizing ultrasound measurements or piezoelectric devices. Other than accuracy problems, it is assumed that such devices did not gain much acceptance due to their intrusive nature, which interrupts the intimacy and simplicity of the mother/infant feeding and bonding process.

Other proposals include weighing the mother and/or infant or measuring the fullness of the infant's stomach before and after nursing, as disclosed, for example, in U.S. Patent Application Publication No. 2008/0097169 to Long, et al., U.S. Patent Application Publication No. 2008/0077040 to Ales, et al., and U.S. Patent Application Publication No. 2008/0077042 to Feldkamp, et al. Such proposals involve a substantial degree of inconvenience, which may explain their lack of widespread acceptance. In addition, experimental data suggests that weighing is an imprecise method for assessing milk intake in young infants. See O. E. M. Savenije, P. L. P. Brand, "Accuracy and precision of test weighing to assess milk intake in newborn infants", Arch Dis Child Fetal Neonatal (2006) 91:F330-F332.

Very commonly, pediatricians and nurses simply instruct worried mothers to count the number of wet (by urine) diapers per day, as some indication of the amount of breast milk suckled by the infant. 1-5 wet diapers per 24 hours during the infant's first week of life, and 6 or more wet diapers per 24 hours for older infants, is a rate commonly suggested by caregivers as indicating sufficient breast milk intake. Naturally, however, this diaper counting cannot be regarded as exact science, mainly since it does not provide a concrete measurement of actual volume of urine secretion per 24 hours.

Accordingly, there is still a long felt need for unobtrusive, convenient devices and methods of estimating the quantity of breast milk suckled by an infant.

Applicant's PCT Patent Application No. PCT/IB2012/052648, filed May 25, 2012, discloses devices, systems and methods for sensing the well-being of a subject, by detecting one or more physiological parameters. Applicant's PCT Patent Application No. PCT/IL2011/000615, filed Jul. 28, 2011, discloses system and methods for monitoring physiological conditions of a subject. These patent applications are incorporated herein by reference in their entirety.

SUMMARY

The following embodiments and aspects thereof are described and illustrated in conjunction with systems, tools and methods which are meant to be exemplary and illustrative, not limiting in scope.

There is provided, in accordance with an embodiment, a sensor for indirect estimation of breast milk intake by an infant, the sensor comprising: a housing configured to be externally attached to an incontinence product worn by a subject, said housing comprising: a light-emitting diode (LED) configured to illuminate the incontinence product; a photodetector configured to output an indication of the amount of light reflected from the incontinence product; and an integrated circuit configured to: (a) receive the indication from said photodetector, (b) compute, based on the indication, an amount of urine secreted by the subject into the incontinence product, and (c) estimate the amount of breast milk intake by the infant based on the amount of urine secreted by the subject into the incontinence product.

There is further provided, in accordance with an embodiment, a urine sensor comprising: a housing configured to be externally attached to an incontinence product worn by a subject, said housing comprising: a light-emitting diode (LED) configured to illuminate the incontinence product; a photodetector configured to output an indication of the amount of light reflected from the incontinence product; and an integrated circuit configured to: (a) receive the indication from said photodetector, and (b) compute, based on the indication, an amount of urine secreted by the subject into the incontinence product.

In some embodiments, said LED is a white-light LED.

In some embodiments, said LED is an infrared LED.

In some embodiments, said photodetector is a light-dependent resistor (LDR).

In some embodiments, the indication of the amount of light is a decline in voltage.

In some embodiments, the decline in voltage corresponds to an increase in the amount of urine in the incontinence product.

In some embodiments, the indication of the amount of light is an increase in voltage.

In some embodiments, the increase in voltage corresponds to a decrease in hydration of the subject.

In some embodiments, said integrated circuit is further configured to estimate a hydration level of the subject, based on a detection of a shade of the urine secreted by the subject into the incontinence product.

In some embodiments, said integrated circuit is further configured to estimate the hydration level of the subject based on a synergistic analysis of the shade of the urine and the amount of the urine.

In some embodiments, said housing further comprises a sticker for external attachment to the incontinence product.

In some embodiments, said housing further comprises a Velcro for external attachment to the incontinence product.

In some embodiments, said housing further comprises a clip for external attachment to the incontinence product.

In some embodiments, said housing further comprises a screen operative couple to said integrated circuit, wherein said screen is configured to display the amount of urine.

In some embodiments, said housing further comprises a screen operatively coupled to said integrated circuit, wherein said screen is configured to display the estimated amount of breast milk intake.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIGS. 3A-G show a front isometric view, a front plan view, a back plan view, a right side view, a left side view, a top view and a bottom view of an exemplary sensor, according to some embodiments.

DETAILED DESCRIPTION

Devices and methods useful for indirect estimation of breast milk intake by an infant are disclosed herein. According to present embodiments, the amount of urine secreted into the infant's diaper is measured, and may be used to estimate if a sufficient amount of breast milk is suckled by the infant. This estimation may be used instead of or together with the wet diaper counting method discussed above. The counting method may be enhanced if an indication of a wet diaper, and the amount of urine in that wet diaper, is given, because if the infant's caregiver is unaware of these factors, he or she may change diapers only after a diaper accumulates multiple urinations, leading to a false lower count of wet diapers and to groundless worry.

Advantageously, the amount of urine is detected using a sensor which is mounted on the infant's diaper externally, and therefore does not come in direct contact with the urine or with the infant's body. The advantageous sensor allows for convenient, non-intrusive measurement of urine secretion, in a manner which does not interfere with the intimacy and simplicity of the mother/infant feeding and bonding process. In alternative embodiments, the sensor is embedded within the diaper itself.

In some embodiments, the sensor is used for measuring the amount of urine secreted into an incontinence product, such as an adult diaper or an infant diaper, for purposes unrelated to breastfeeding. For example, the sensor may be used in scenarios requiring fluid management of a subject, to detect renal failure, to estimate hydration, and/or the like.

According to some embodiments, the same or a different sensor, configured to estimate a subject's hydration level is provided. The sensor detects the shade of the urine, which is known to be indicative of the level of hydration. Generally, the darker the urine, the more dehydrated the subject is, and vice versa. Transparent urine usually means a good hydration level. Optionally, the sensor also measures the amount of urine secreted, so that it estimates the level of hydration using a combination of two factors: amount and shade.

The terms "diaper", "incontinence product" and "absorbent incontinence product" may be used here interchangeably, and relate to a wearable product having a layered construction, which allows the transfer and distribution of urine to an absorbent core structure where it is locked in. Similarly, the term "infant" is used here for convenience only, and may relate to any subject, such as a baby, a child or an adult.

Figure 1:
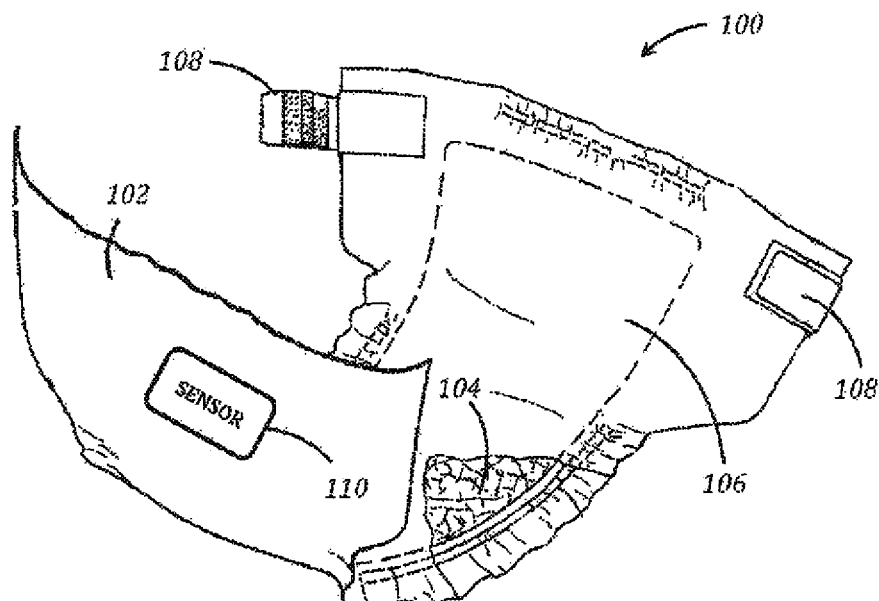
FIG. 1 shows a characteristic layered diaper with a sensor according to some embodiments.
Figure 2:
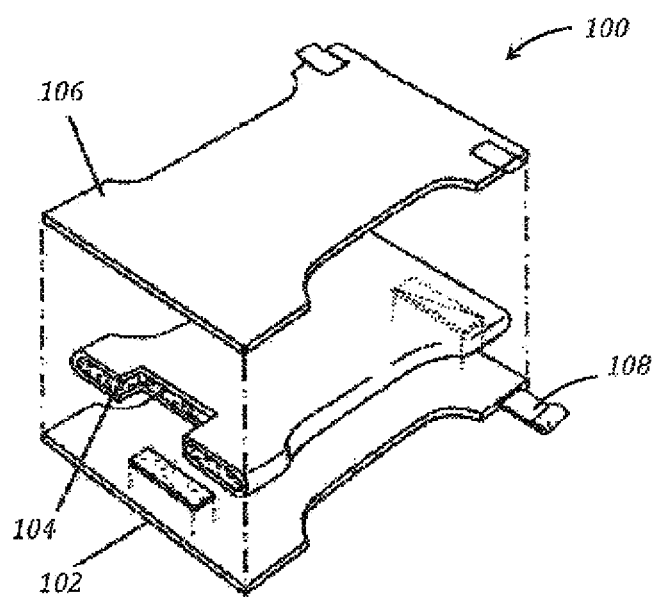
FIG. 2 shows a cross-sectional view of layers forming that diaper.
Figure 3D:
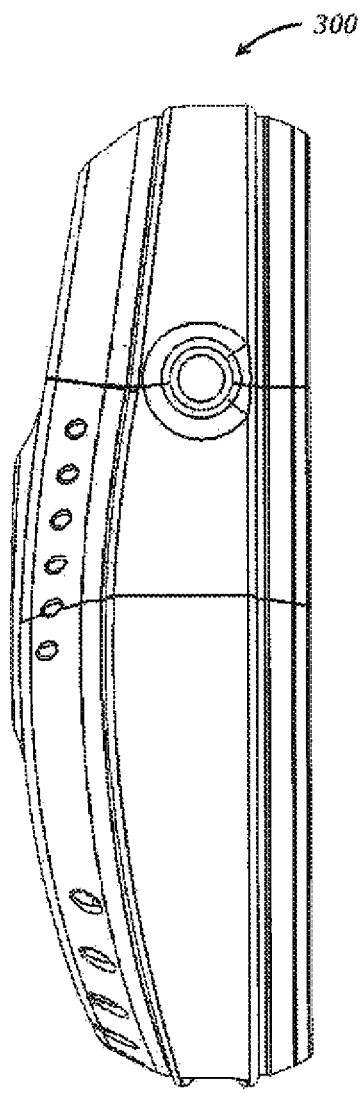
Figure 3E:
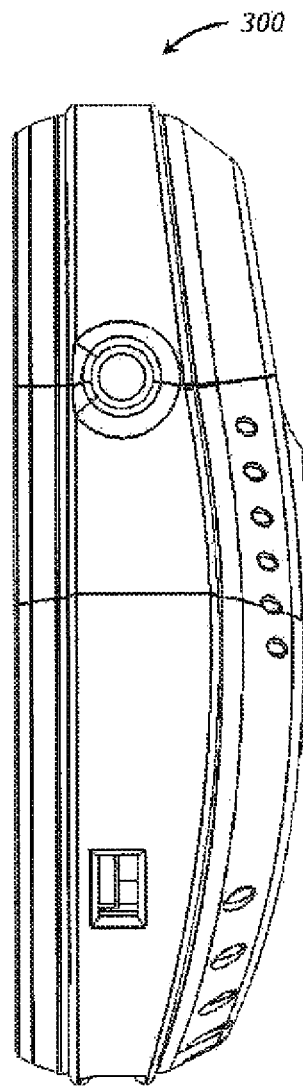
Figure 3F:
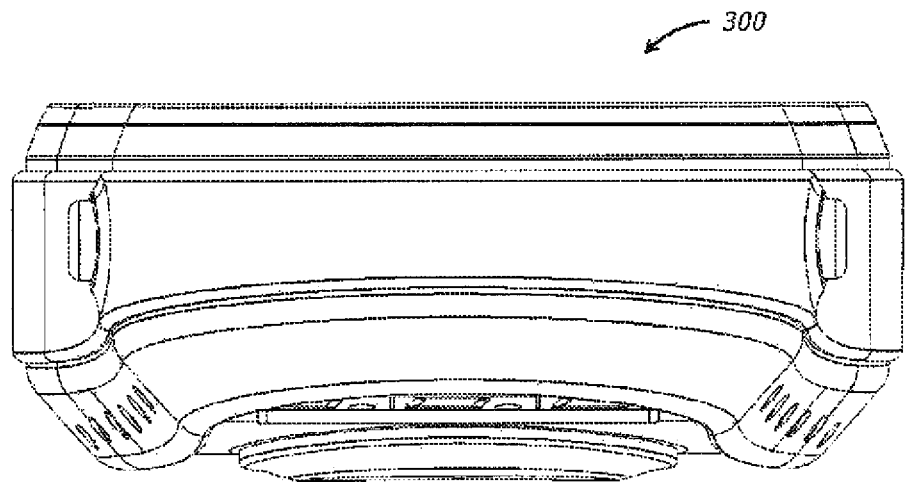
Figure 3G:
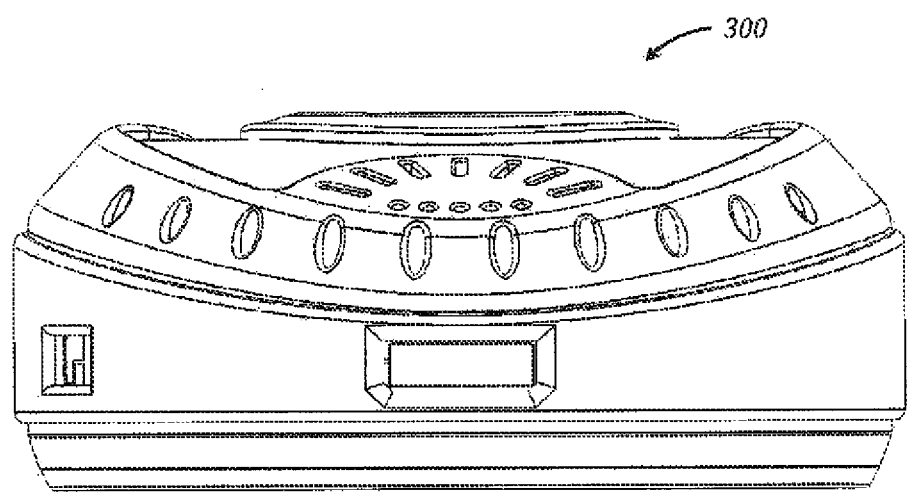

Reference is now made to FIG. 1, which shows a characteristic layered diaper 100 in a perspective view, and to FIG. 2, which shows a cross-sectional view of layers forming the same diaper. The basic layers found in many modern diapers, such as diaper 100, are commonly: (a) an outer shell 102, commonly made of a breathable polyethylene film or a nonwoven and film composite, which prevents wetness and soil transfer to the outside environment; (b) an inner absorbent layer 104, usually containing a mixture of air-laid paper and superabsorbent polymers; and (c) a layer 106 nearest the skin, oftentimes made of a nonwoven material with a distribution layer directly beneath, which transfers wetness to the absorbent layer. A pair of fasteners 108 is commonly used to close the diaper around the wearer's abdomen.

In some embodiments, a sensor, such as sensor 110, may be attached, as an external add-on, to outer shell 102 of diaper 100. In some embodiments (not shown), the sensor may be embedded in or integrally formed with outer shell 102. In some embodiments (not shown), the sensor may be embedded in or integrally formed with inner absorbent layer 104. In some embodiments, the one or more sensors may be embedded in or integrally formed with the layer 106 nearest the skin. The positioning of sensor 110 is shown here merely as an example. A sensor may nonetheless be positioned in or on any of the diaper's layers, and/or at a different area of the diaper; in addition, components of the sensor may be distributed in different layers and/or in different positions.

A photodetector may be used, in the sensor, for measuring the amount of urine secreted into a diaper. There are multiple varieties of photodetectors (also "light sensors") which may be suitable, such as photoresistors (LDRs), photovoltaic cells, photodiodes (operative in photovoltaic mode or photoconductive mode), IR sensor, phototransistors, CCD (charge coupled device), CMOS (complementary metal oxide semiconductor) and/or the like An exemplary sensor 300, for use in infants and/or other persons in need thereof, is shown in FIGS. 3A-G in a front isometric view, front plan view, back plan view, right side view, left side view, top view and bottom view, respectively. Sensor 300 may include a housing encompassing internal components, such as a photodetector, an illuminator (e.g. LED), an integrated circuit (IC) and/or the like. The housing may be attached to the wearer's garment, such as a diaper, by way of a sticker, Velcro and/or the like, which may be positioned, for example, on the back side of the housing. Additionally or alternatively, the housing may be attached to the garment using a clip and/or other means known in the art (not shown).

The IC of sensor 300 may measure the amount of urine secreted into a diaper, using, for example, a photodetector, as discussed above. The photodetector outputs an indication of the amount of light reflected from the diaper. The indication is received by the IC which computes the amount of secreted urine based on the indication. The photodetector may receive light through an aperture in the housing, and the LED, which is optional, may illuminate the garment through an optional LED aperture. One or both apertures may be open, or closed with a cover transparent enough to allow the transfer of light. Namely—the apertures are visually-exposed at the back side of the housing. The cover may be, for example, the Velcro, adhesive or a different means for attaching sensor 300 to the garment. An optional IR transceiver may be positioned at or near an IR hole.

It should be noted that some or even all sensors, transceivers, illuminators and/or the like may be positioned under the Velcro, adhesive or the different means for attaching sensor 300 to the garment, or even inside the housing with no exposure to the environment. This may provide protection for the sensors/illuminators while avoiding the need to provide visible holes in the housing. It may also provide sealing of the housing, either completely or partially.

The LED may be a white-light LED, a red-light LED, an infra-red LED or a LED of a different wavelength.

A screen of sensor 300 may be operatively coupled with the IC, to indicate the amount of urine measured and/or the amount of breast milk intake. The amount of breast milk intake indicated by the screen may be equal, as one example, to the amount of urine; these two amounts are known to be similar. Additionally or alternatively, the IC may display on the screen a simple indication of a urination event, in the form of an alert. The alert may be issued when the sensor detects at least a predetermined amount of urine, e.g. at least 10 cc, at least 15 cc, at least 20 cc, at least 30 cc or any other predetermined amount programmed into the IC.

The alert may indicate to a caregiver that the subject wearing the diaper has urinated. The caregiver may then use the wet diaper counting method discussed above, to know if the breast milk intake by the subject is sufficient. The indication on the screen may be, for example, numerical—showing the number of milliliters (or a different unit) measured. Additionally or alternatively, a multi-level scale may be displayed, where each level in the scale is indicative of a different amount of urine. Additionally or alternatively, sensor 300 may include a speaker, a buzzer, and/or the like, for issuing audible indication of the amount of urine.

Alternatively or additionally, the alert may indicate to a caregiver that the hydration level of the subject wearing the diaper has fallen below a threshold level. The alert may be issued when the sensor detects at least a predetermined shade of urine programmed into the IC.

Figure 4:
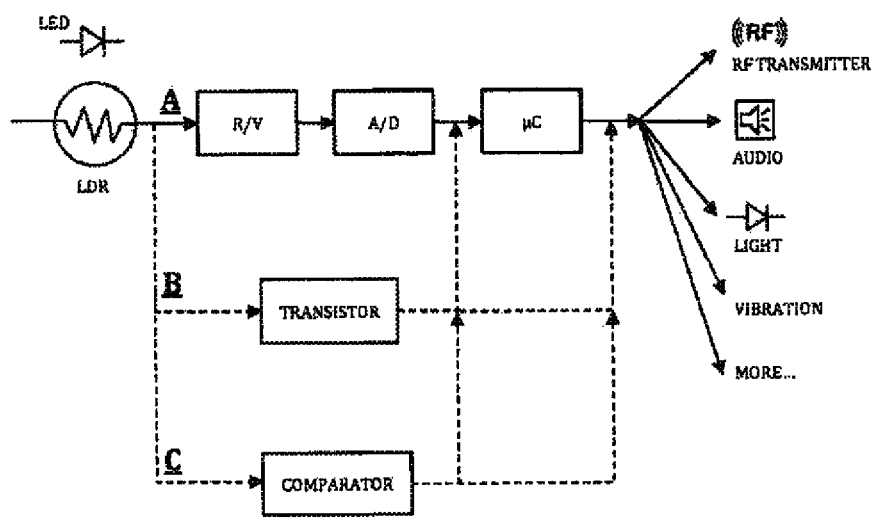
FIGS. 4 and 5 show block diagrams of an electronic circuit of a sensor, according to some embodiments.
Figure 5:
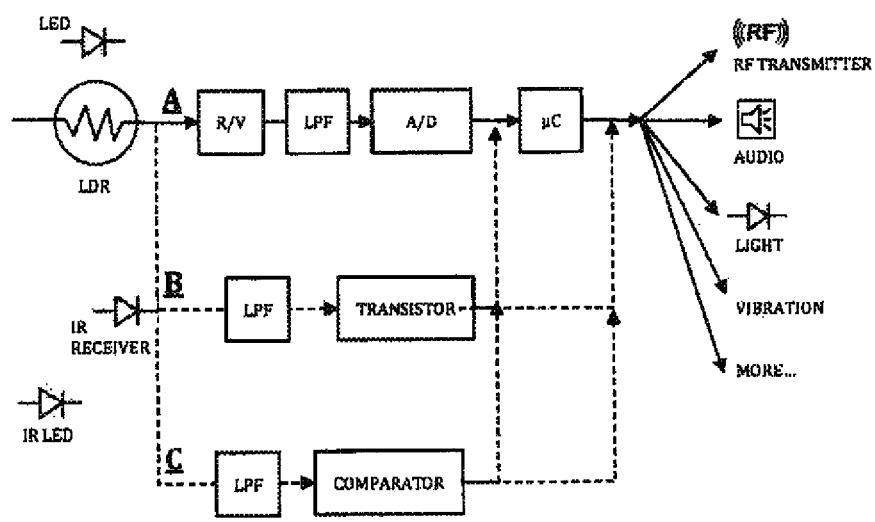
Figure 6:
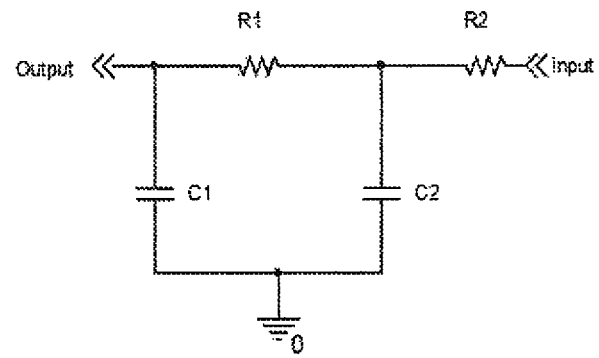
FIG. 6 shows a circuit diagram of a low-pass filter, according to some embodiments.

Voltage fluctuations in the output of the photodetector, resulting from the infant's movement and activity, may make the urine amount measurement more complex. Advantageously, software and hardware low-pass filters (LPFs) incorporated in the IC, which were tested separately, were able to make the signal outputted by the photodetector more parabolic and softer, making the urine amount measurement possible using the methods and algorithms discussed here. The LPFs were based on a moving average calculation. FIG. 5 shows an alternative to FIG. 4, using LPFs. FIG. 6 shows an exemplary $2^{nd}$-order LPF circuit, although those of skill in the art will recognize that an LPF of a different order and/or topology may be suitable.

Reference is now made back to Figs. FIGS. 3A-G. Optionally, sensor 300 includes a piezoelectric sensor (not shown) for detecting the breathing of the wearer. The piezoelectric sensor may be a PVDF sheet positioned inside or external to the housing, advantageously without contacting the wearer's body directly, and optionally not even through any flexible member, such as a membrane, which is sometimes used in the art for mechanically transferring motion or pressure from an object to a PVDF sheet. The PVDF sheet may be located, for example, on the internal surface of the back side of the housing. The PVDF sheet is optionally in contact with the housing. Alternatively, the PVDF sheet may be mounted inside the housing without contacting it. Further alternatively, a slightly depressed area in the housing may house the PVDF sheet externally to the housing, which depressed area may be covered by the Velcro, adhesive or the like as discussed above.

Sensor 300 may further include a potty training functionality, configured to enhance the common infant potty training procedure. A parent or another caregiver may record one or more voice messages, in his or hers own voice, to be automatically played using a speaker when sensor 300 senses secretions. The voice message(s) may, for example, remind the infant that the potty should have been used, thereby providing immediate biofeedback to unintentional secretion. Optionally, to make sensor 300 more appealing to the infant, it may automatically play a pre-recorded voice message when touched by the infant.

Voice messages may be pre-recorded in the factory and/or recorded by the parents/caregivers. To that end, one or more buttons, such as a record button and/or a play button may be provided in sensor 300. Optionally, one or more status lights and/or a screen (such as an LCD screen) may signal to the person recording that the recording has begun, ended and/or the like.

Optionally, either before, after or during the playing of any of such voice message, an acoustic signal may be emitted by sensor 300, to transmit an indication of the detected secretion to a remote or receiving device, as will be discussed below. Further optionally, the indication may trigger the loading and/or playing of an educational video clip on potty training on the remote or receiving device, which the parent and child can watch together or separately.

Further optionally, a potty may include an acoustic or a radio frequency receiver, so that when an indication of a fecal and/or urinary secretion event is received at the potty, the potty may urge the infant to use it, by emitting light, sound and/or the like. The indication may be received from sensor 300 and/or from the remote or receiving device.

According to some embodiments, the sensor disclosed herein may further interface and/or communicate with an external and/or remote device to convey a signal generated by the sensor(s) disclosed herein to the device (herein, a "receiver" or a "receiving device"). Conveying the signal from the sensor of the sensing device to the receiving device may be performed by various communication routes, such as radio frequency or acoustic communication.

Acoustic communication makes use of sound and/or ultrasound, whereby a "transmitter" produces a sound that is detected by a "receiver". Sound is produced by the transmitter when a physical object vibrates rapidly, disturbs nearby air molecules (or other surrounding medium) and generates compression waves that travel in all directions away from the source. Sound can be made to vary in frequency (high pitch vs. low pitch), amplitude (loudness), and periodicity (the temporal pattern of frequency and amplitude). Since acoustic waves move rapidly through the medium, acoustic signals can be quickly started, stopped, or modified to send a time-sensitive message.

According to some embodiments, for each of the various physiological conditions detected by the sensing devices and systems as disclosed herein, a different acoustical signal may be generated by one or more transducers connected to the microcontroller. The various acoustical signals may differ by various parameters, such as, but not limited to: frequency, periodicity, amplitude, duration, series of signals and the intervals therebetween (duty cycle) and/or the like. The frequency of the acoustic alert may be in any range. In an embodiment, the acoustic alert is in the range of 1 Hz to 10 KHz. In another embodiment, the acoustic alert is in the range of 10 Khz to 18 Khz. In another embodiment, the acoustic alert is in the range of 18 KHz to 20 Khz. In another embodiment, the acoustic alert is in the range of 18 KHz to 22 Khz. In another embodiment, the acoustic alert is in the range of 20 KHz to 22 Khz. In another embodiment, the acoustic alert is higher in the ultrasonic range, such as above 22 KHz.

For example, if the device's sensor detects urine, it may produce an 8 KHz tone, optionally in conjunction with other series of tones. For example, if the device sensor detects feces, it may produce an 8 KHz tone, optionally in conjunction with other series of tones. As another example, if the device's sensor detects high temperature it may produce a 5 Khz tone, optionally in conjunction with other series tones. As yet a further example, if the device's sensor detects a breathing problem, it may produce a 20 Khz tone, optionally in conjunction with other series of tones. These were simplistic examples, meant merely to demonstrate how acoustic communication may be realized.

According to further embodiments, the acoustical signal produced by the sensing device may be received by a receiving device, which is equipped with a microphone. Various acoustic communication protocols may be used for establishing an acoustic communication between the transmitter (the sensor) and the receiving device. For example, a publication entitled "*Multi-User Frequency Hopping Underwater Acoustic Communication Protocol*", Woods Hole Oceanographic Institution, Woods Hole, Mass. 02543, May 25, 2000, the contents of which is incorporated by reference in their entirety, discloses an exemplary acoustic communication protocol in which data "packets", similar in concept to those used in IP communications, are produced using acoustic waves.

According to some embodiments, the receiving device may include any type of device configured to receive an acoustic signal via the appropriate acoustic communication protocol, and may further convey the signal to a user, who may be located in a remote location. An added benefit of such a setting is that acoustic communication, unlike radio frequency communication, does not involve electromagnetic radiation in the subject's area, thereby increasing the safety of use of the devices and systems disclosed herein.

According to some embodiments, the acoustic tone or set of tones which may be generated by the sensing device define an acoustic protocol in the time domain. In some embodiments, the protocol may be programmed in the sensing device's microcontroller and in the receiving device.

According to some embodiments, an exemplary acoustic protocol may include the following "packets": (1) start bit, get ready for tone sequence; (2) first tone; (3) second tone; (4) $N^{th}$ tone; (5) stop bit, tone sequence stopped. Any of the steps and the time length, number of bits and frequency of the bit tone, loops, and the like, may be changed to define an appropriate protocol.

Figure 7:
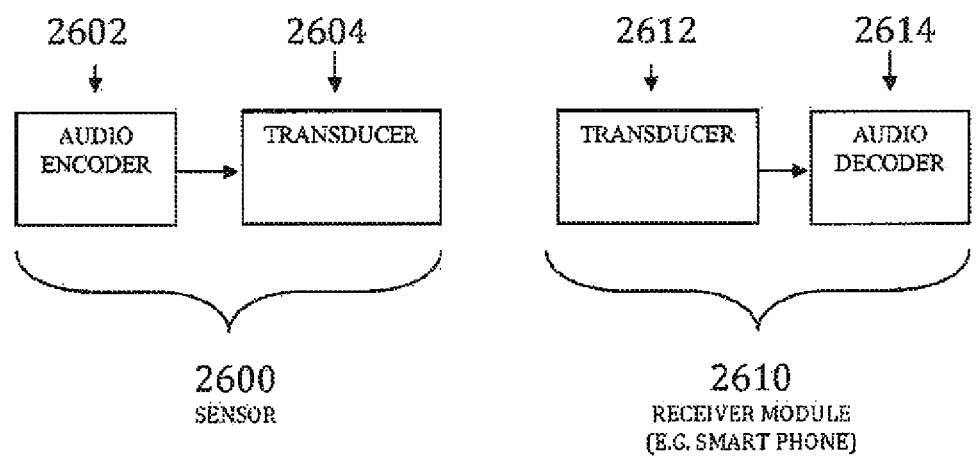
FIG. 7 shows an exemplary acoustic communication interface, according to some embodiments.

Reference is now made to FIG. 7, which schematically illustrates an exemplary acoustic communication interface between a sensing device and a receiving device. Sensing device 2600 includes an audio encoder 2602, adapted to produce an acoustic signal based on the signal produced by the sensor. Audio encoder 2602 may be incorporated in the microcontroller discussed earlier, or be connected to it. The sensing device further includes a transducing element 2604, adapted to convert an electrical signal from audio encoder 2602 into an acoustic signal transmitted towards the remote receiver. In some exemplary embodiments, the transducing element 2604 is a speaker. The acoustic signal produced by the sensing device may then be detected by transducer unit 2612 of receiving device 2610. In some exemplary embodiments, transducer 2612 is a microphone. The acoustic signal may then be decoded by audio decoder 2614 of the receiving device. Decoding the acoustic signal may be used to convert the acoustic signal to an electrical signal. The decoded signal may be processed and conveyed to a user. In some embodiments, the decoded signal may be converted to an alarm signal that may a visual signal, a tactile signal, an audible signal, and the like, or any combination thereof.

According to some embodiments, the receiving device may be portable. In some embodiments, the receiving device may be placed in the vicinity of the sensing device. In some embodiments, the receiving device may be place at a remote location, but still in acoustic communication range from the transmitting device. In some exemplary embodiments, the receiving device is a smart phone. In some exemplary embodiments, the receiving device is configured to communicate with a smart phone.

Figure 8:
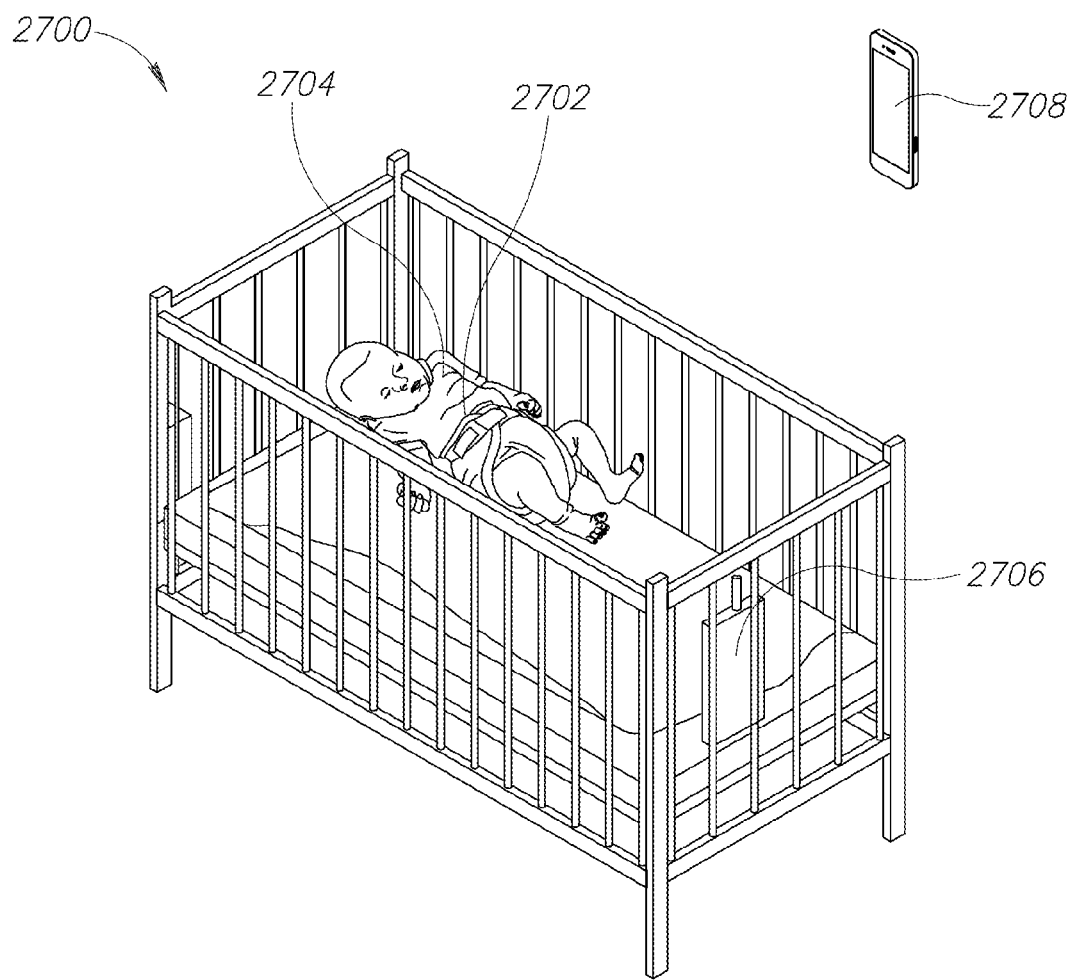
FIG. 8 shows an acoustic interface of a sensing system, according to some embodiments.

Reference is now made to FIG. 8, which schematically illustrates an acoustic interface of a sensing system, according to some embodiments. As shown in FIG. 8, in a system 2700, a sensing device 2702 is placed on a subject (exemplary baby 2704). When an event is detected by the sensor of the sensing device, an acoustic alert is produced by the sensing device. The acoustic alert is detected by a receiving device such as receiving device 2706, which is located in the proximity of the subject. The receiving device may then issue an alert (such as audible, tactile and/or visual alert) to a supervisor. Additionally or alternatively, the receiving device may serve as a relay station configured to communicate with a remote device (such as smart phone 2708), which is, in turn, configured to generate an appropriate alarm to the supervisor.

In some embodiments, the receiving device is configured to communicate with the remote device via the Internet and/or via short-range radio, utilizing technologies such as WiFi, Bluetooth, SMS, cellular data communication, push notification protocol, and activate the alarm therein, in order to notify a supervisor which may be located in a remote location. The remote device may execute an application for communicating with the receiving device and to produce audible and/or visual alarm and/or tactile alarms.

In an implementation successfully experimented with by the inventor, an Apple iPhone 4 smart phone (hereinafter "iPhone") was used as the receiving device. The iPhone's microphone picked up the acoustic signals which were emitted by the sensing device from a range of approximately 10 meters with no walls in between or from a lower range if walls existed, and then transmitted an alert via Apple's push notification service (APN) to another iPhone acting as the remote device.

The Apple Push Notification service is intended to relay messages to iDevices even when a target application on the receiving device is not running. The APN transports and routes a notification from a given provider to a given device. A notification is a short message consisting of two major pieces of data: the device token and the payload. The device token contains information that enables the APN to locate the device on which the client application is installed. The APN also uses it to authenticate the routing of a notification. The payload is a JSON-defined property list that specifies how the user of an application on a device is to be alerted. The flow of remote-notification data is one-way. The provider composes a notification package that includes the device token for a client application and the payload. The provider sends the notification to the APN which, in turn, pushes the notification to the device.

Figure 9:
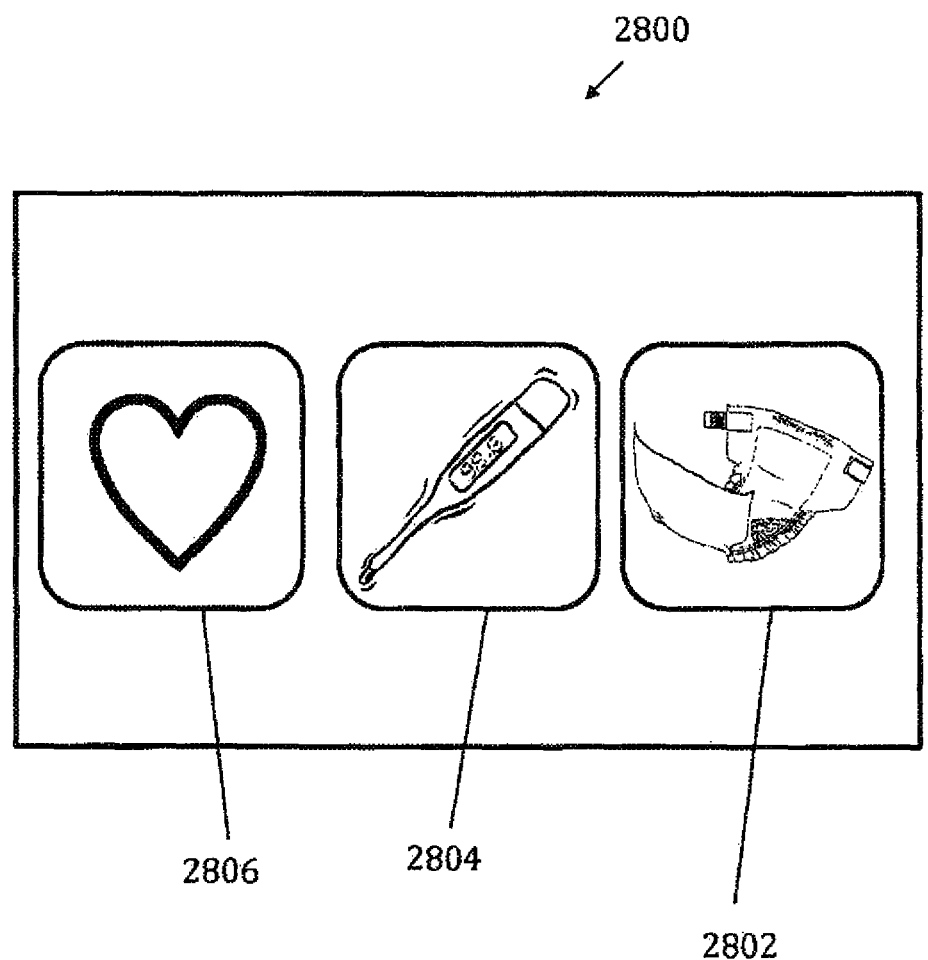
FIG. 9 shows a graphic interface, according to some embodiments.

The message received by the iPhone acting as the remote device included information describing the event detected by the sensing device. The user was provided with the option of triggering the opening of the inventor's mobile application installed on this iPhone, which displayed the alert more visually. The application produced an audible, a tactile and/or a visual alarm. In some embodiments, the visual alarm is a graphical animation (shown for example in FIG. 9). For example, if urine is detected by the sensing device, an appropriate acoustic signal is generated. The acoustic signal is received by the receiving device (such as, for example, a smart phone, 2800) in which a visual and audio alarms, in the form of an animation of a diaper, changes its color to blue (2802), in conjunction with water/splash sound are produced by the smart phone. Additionally or alternatively, the receiving device may relay information regarding the detection to the remote device, in which a visual and audio alarms are activated. As another example, if feces are detected, a visual and audio alarms in the form of an animation of a diaper changes its color to brown, in conjunction with gas sounds are produced by the smart phone. For example, if high body temperature is detected by the sensing device, a visual and audio alarms in the form of an animation of a thermometer changing its color to green (2804) in conjunction with boiling sound is produced. Finally, if a breath rate problem is detected by the sensing device, a visual and audio alarm in the form of an animation of a still heart (2806) in conjunction with ambulance sound is produced.

More details on Apple's Push Notification service and related issues is available online at Apple's iOS Developer Library, http://developer.apple.com/library/ios/navigation/, which is incorporated herein by reference in its entirety.

Examples and Experimental Results

In a series of experiments conducted by the inventor, the measurement of urine amount in a diaper, as well as the detection of urine shade in a diaper, have been tested and verified. The experiments discussed below include devices and methods which form embodiments of the present invention.

Figure 10A:
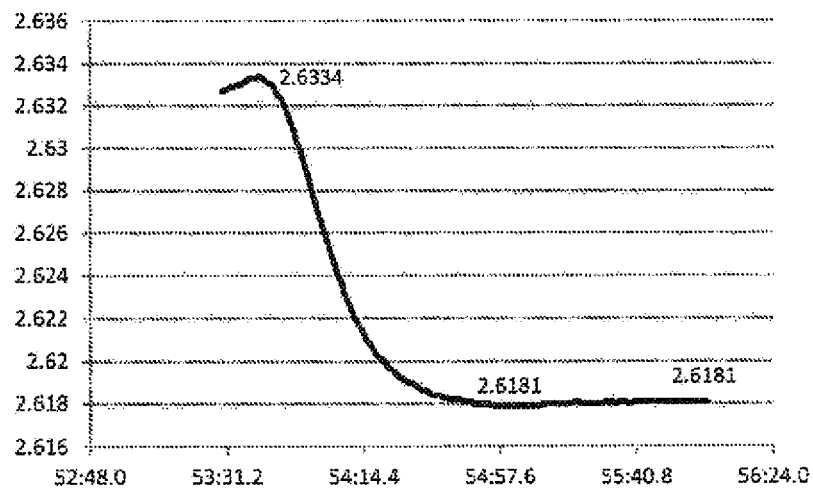
FIGS. 10A, 10B and 10C show graphs of sensor readings, according to some embodiments.
Figure 10B:
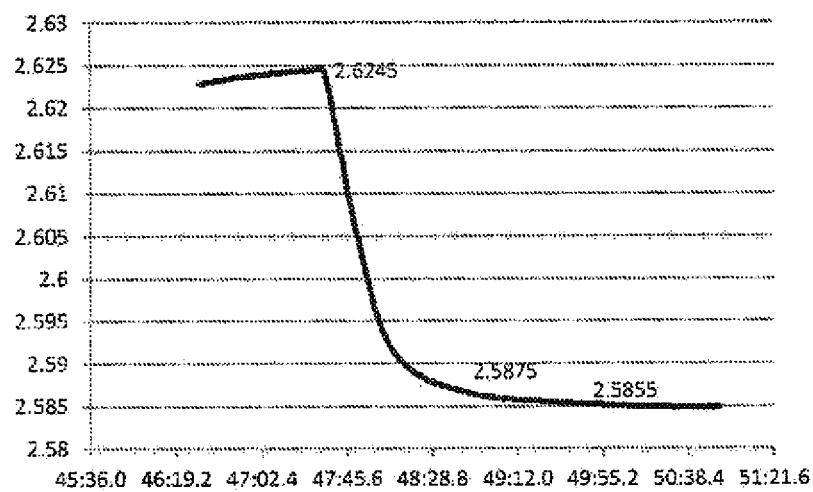
Figure 10C:
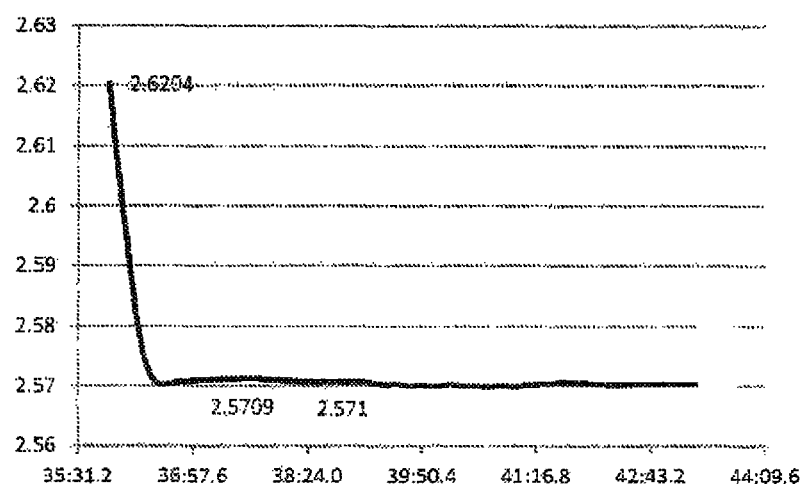

In a first experiment, a sensor including an LDR and a LED illuminator was used. The LDR was PerkinElmer Optoelectronics VT900. However, LDRs of different models are explicitly intended herein. Optionally, the LDR in some embodiments is configured to sense light in approximately the visible spectrum, also referred to as "ambient light". The illuminator, namely—the LED in this example, is an essentially white LED. The sensor was attached externally to a Pampers Active Baby size 3 diaper worn by a baby-shaped doll. The sensor was attached to the front area of the diaper, over the lower abdomen of the doll. The experiment was repeated three times: once with injection of 10 milliliters (ml) of water into the diaper, once with injection of 20 ml, and once with injection of 30 ml. Sensor readings were approximately linearly correlated with the amount of water, which simulated urine. FIGS. 10A, 10B and 10C show graphs of sensor readings for the 10 ml, 20 ml and 30 ml injections, respectively. The Y-axis in these figures denotes voltage output of the photodiode, and the X-axis denotes time in minutes and seconds. As shown, the injecting of water (equivalent to urination) results in a rapid decline in voltage. In the 10 ml injection, the voltage difference between a pre-injection baseline and a plateau reached between approximately 30 seconds and 120 seconds post-injection, was 11 millivolt (mV). In the 20 ml injection, the difference was 38 mV, and in the 30 ml injection 68 mV. In other words, each 10 ml addition from the initial 10 ml is exhibited, essentially linearly, in an additional drop of about 30 mV.

In a second experiment, a sensor including an IR sensor was used. The IR sensor was a Fairchild QRE1113GR.

Figure 11A:
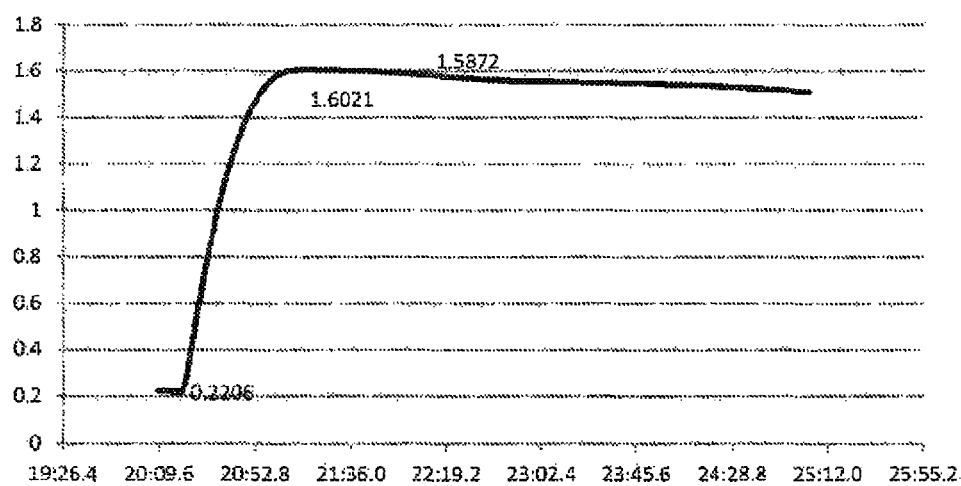
FIGS. 11A and 11B show graphs of sensor readings, according to some embodiments.
Figure 11B:
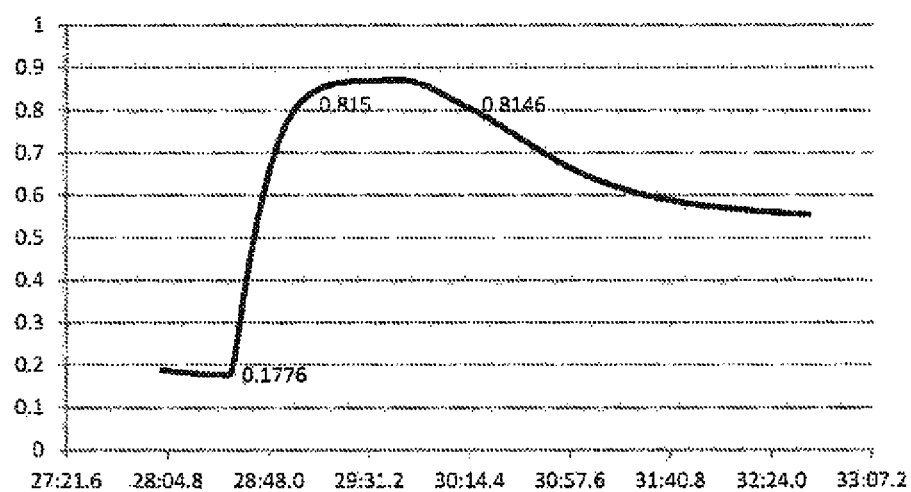

The IR sensor was attached externally to a Pampers Active Baby size 3 diaper worn by a baby-shaped doll. The sensor was attached to the front area of the diaper, over the lower abdomen of the doll. The experiment was repeated multiple times, with injection of liquids imitating urine of different shades—from clear (water) to relatively dark yellow (apple syrup). FIGS. 11A and 11B show graphs of sensor readings for clear (pure water) liquid injection and of dark yellow (apple syrup) liquid injection, respectively. The Y-axis in these figures denotes voltage output of the photodiode, and the X-axis denotes time in minutes and seconds. As shown, the injecting of either liquid results in a rapid increase in voltage, followed by a slower decay. The difference between the pre-injection baseline and a post-injection peak (which occurred after about 1 minute) was 1.382 Volts for the water, and 0.637 Volts for the apple syrup.

In additional experiments (graphs thereof are not shown), intermediate levels of liquid darkness were used, resulting in approximately linear changes in voltage. In conclusion, this method is reliable in determining the hydration level of a subject based on his or her urine shade.

Another example for a suitable sensor adapted to detect the shade of urine is a TCS3404 digital color sensor by Texas Advanced Optoelectronic Solutions, Inc. The TCS3404 includes an 8×2 array of filtered photodiodes, analog-to-digital converters, and control functions on a single monolithic CMOS integrated circuit. Of the 16 photodiodes, 4 have red filters, 4 have green filters, 4 have blue filters, and 4 have no filter (clear).

Yet a further example of a suitable sensor adapted to detect the shade of urine is the ALS-PT19-315C ambient light sensor manufactured by Everlight Electronics Co., Ltd.

Optionally, a sensor for urine quantity measurement and a sensor for urine shade measurement are used together, in a same housing, so as to both indicate the amount of secreted urine and the hydration level. Alternatively, a single sensor, whose voltage (or other) readings are indicative of both urine quantity and shade, may be used. Advantageously, knowing both the urine's quantity and its shade enables a processor of the sensor(s) to synergistically analyze estimate the level of hydration. For example, if the urine's shade is relatively dark, but its amount over a certain duration is relatively large, then it is likely that the subject is not substantially dehydrated. In contrast, a small quantity of light-colored urine may still be indicative of dehydration.

Some embodiments may be implemented, for example, using a non-transitory computer-readable medium or article which may store an instruction or a set of instructions that, if executed by a sensor comprising a hardware processor, cause the sensor to perform a method and/or operations in accordance with embodiments of the invention. Such a sensor may include, for example, any suitable processing platform, computing platform, computing device, processing device, computing system, processing system, computer, processor, or the like, and may be implemented using any suitable combination of hardware and/or software. The computer-readable medium or article may include, for example, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The instructions may include any suitable type of code, for example, source code, compiled code, interpreted code, executable code, static code, dynamic code, or the like, and may be implemented using any suitable high-level, low-level, object-oriented, visual, compiled and/or interpreted programming language, such as C, C++, C#, Java, BASIC, Pascal, Fortran, Cobol, assembly language, machine code, or the like.

In the description of the application, each of the words "comprise", "include" and "have", and forms thereof, are not necessarily limited to members in a list with which the words may be associated.

What is claimed is:

1. A device, comprising:
    a housing configured to be externally attached to an incontinence product worn by a subject, wherein the housing comprises:
        (a) a first sensor comprising:
            (i) a first light-emitting diode (LED) configured to illuminate a portion of the incontinence product;
            (ii) a first photodetector configured to output an indication of an amount of light reflected from the portion of the incontinence product illuminated by the first LED; and
            (ii) a first integrated circuit, configured to receive the indication from the first photodetector, and compute, based on the indication from the first photodetector, an amount of urine in the incontinence product; and
        (b) a second sensor comprising:
            (i) a second light-emitting diode (LED) configured to illuminate a portion of the incontinence product;
            (ii) a second photodetector configured to output an indication of the amount of light reflected from the portion of the incontinence product illuminated by the second LED; and
            (iii) a second integrated circuit, configured to receive the indication from the second photodetector, and compute, based on the indication from the second photodetector, a hydration level of the subject.

2. The device of claim 1, wherein the subject is an infant.

3. The device of claim 2, wherein the device provides an indirect estimate of breast milk intake by the infant.

4. The device of claim 2, wherein the first integrated circuit is further configured to issue an alert if the amount of urine in the incontinence product exceeds a predetermined threshold, thereby confirming adequate breast milk intake by the infant.

5. The device of claim 1, wherein the first LED is a white-light LED.

6. The device of claim 1, wherein the second LED is an infrared LED.

7. The device of claim 1, wherein the first photodetector is selected from the group consisting of: photoresistors, photovoltaic cells, photodiodes, infrared sensors, phototransistors, CCDs (charge coupled devices), and CMOS (complementary metal oxide semiconductors).

8. The device of claim 7, wherein the first photodetector is a light-dependent resistor (LDR).

9. The device of claim 1, wherein the second photodetector is selected from the group consisting of: photoresistors, photovoltaic cells, photodiodes, infrared sensors, phototransistors, CCDs (charge coupled devices), and CMOS (complementary metal oxide semiconductors).

10. The device of claim 9, wherein the second photodetector is a light-dependent resistor (LDR).

11. The device of claim 1, wherein the housing further comprises a screen operatively coupled to the first integrated circuit, wherein the screen is configured to display the amount of urine in the incontinence product.

12. The device of claim 1, wherein the housing further comprises a screen operatively coupled to the second integrated circuit, wherein the screen is configured to display the hydration level of the subject.

13. The device of claim 1, wherein the housing further comprises a screen operatively coupled to the first and second integrated circuit, wherein the screen is configured to display the amount of urine in the incontinence product and the hydration level of the subject.

14. The device of claim 3, wherein the housing further comprises a screen operatively coupled to the second integrated circuit, wherein the screen is configured to display the amount of breast milk intake of the infant.

* * * * *